United States Patent [19]

Krüger et al.

[11] Patent Number: 5,250,568

[45] Date of Patent: Oct. 5, 1993

[54] ACYLATED AMINOPHENOL DERIVATIVES

[75] Inventors: Bernd-Wieland Krüger; Klaus Sasse, both of Bergisch Gladbach; Heinz-Wilhelm Dehne, Monheim, all of Fed. Rep. of Germany

[73] Assignee: Bayer Aktiengesellschaft, Leverkusen, Fed. Rep. of Germany

[21] Appl. No.: 900,632

[22] Filed: Jun. 18, 1992

[30] Foreign Application Priority Data

Jun. 25, 1991 [DE] Fed. Rep. of Germany ....... 4120904

[51] Int. Cl.$^5$ .................... A01N 47/06; C07C 67/48
[52] U.S. Cl. ...................... 514/512; 558/248
[58] Field of Search ...................... 558/248; 514/512

[56] References Cited

U.S. PATENT DOCUMENTS

| | | | |
|---|---|---|---|
| 2,923,727 | 2/1960 | Neumoyer | 558/248 |
| 4,486,222 | 12/1984 | Schwartz et al. | 558/248 |
| 4,647,582 | 3/1987 | Takahashi et al. | 514/482 |
| 4,666,943 | 5/1987 | Noguchi et al. | 514/627 |
| 4,939,170 | 7/1990 | Krüger et al. | 514/483 |

FOREIGN PATENT DOCUMENTS 0125901 11/1984 European Pat. Off. ............ 558/248

*Primary Examiner*—Mary C. Lee
*Assistant Examiner*—Joseph K. McKane
*Attorney, Agent, or Firm*—Sprung Horn Kramer & Woods

[57] ABSTRACT

There are described cycloalkyl-carboxanilides of the formula (I)

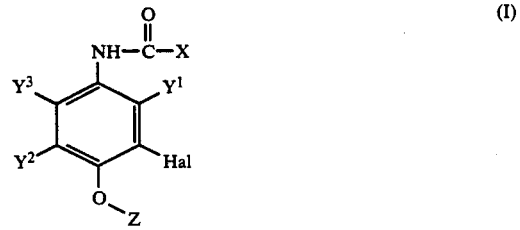

in which X, Hal, $Y^1$, $Y^2$, $Y^3$ and Z have the meaning given in the description, and a process for their preparation.

The compounds of the formula (I) are used for combating pests.

5 Claims, No Drawings

ACYLATED AMINOPHENOL DERIVATIVES

The present invention relates to new cycloalkyl-carboxanilides, a process for their preparation, and their use in combating pests, in particular fungi.

It has been disclosed that certain carbamates have good fungicidal properties (cf. EP 293 718).

Furthermore, there are known a large number of carboxanilides having fungicidal action, in particular a potent action against benzimidazole-tolerant phytopathogens (cf. EP 117,024, EP 125,901, EP 100,615).

Novel cycloalkyl-carboxanilides of the general formula (I)

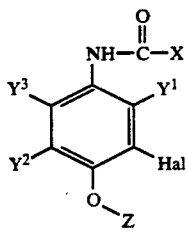

in which
X represents optionally alkyl-substituted cycloalkyl,
Hal represents halogen and
$Y^1$, $Y^2$ and $Y^3$ independently of one another represent hydrogen, halogen, optionally halogen-substituted alkyl, optionally halogen-substituted alkoxy or optionally halogen-substituted alkylthio and
Z represents the group $COSR^1$, where
$R^1$ represents optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl,
have been found.

The substituted cycloalkyl-carboxanilides of the formula (I) contain one or more centres of asymmetry and can thus exist in the form of diastereomers or diastereomer mixtures which are obtained in various ratios. They are mostly obtained in the form of racemates.

Furthermore, it has been found that the new substituted cycloalkyl-carboxanilides of the formula (I)

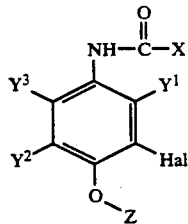

in which
X represents optionally alkyl-substituted cycloalkyl
Hal represents halogen and
$Y^1$, $Y^2$ and $Y^3$ are identical or different and represent hydrogen, halogen, optionally halogen-substituted alkyl, optionally halogen-substituted alkoxy or optionally halogen-substituted alkylthio and
Z represents the group $COSR^1$, where
$R^1$ represents optionally halogen-substituted alkyl, alkenyl, alkoxyalkyl, alkylthioalkyl, polyalkoxyalkyl and optionally substituted cycloalkyl, optionally substituted phenyl, optionally substituted phenylalkyl or substituted phenoxyalkyl,
are obtained when aminophenols of the formula (II)

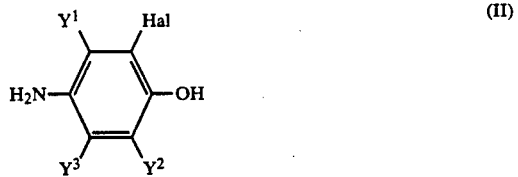

in which Hal, $Y^1$, $Y^2$ and $Y^3$ have the abovementioned meanings, are reacted, in a first reaction step, with carboxylic acid derivatives of the formula (III)

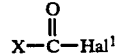

in which
X has the abovementioned meaning and
$Hal^1$ represents halogen, preferably chlorine, or a leaving group customary in the case of acylation reactions, preferably an activating ester radical,
if appropriate in the presence of an acid acceptor and if appropriate in the presence of a solvent or diluent, and these intermediates obtained, of the formula (IV)

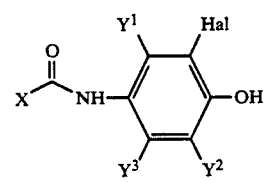

in which X, $Y^1$, $Y^2$, $Y^3$ and Hal have the abovementioned meaning, are then reacted, in a second reaction step, with thiocarbonic acid derivatives of the formula (V)

$$Z-Hal^2 \quad (V)$$

in which
Z has the abovementioned meaning and
$Hal^2$ represents halogen, preferably chlorine, or a leaving group customary in the case of acylation reactions, preferably an activating ester radical,
if appropriate in the presence of an acid acceptor and if appropriate in the presence of a solvent or diluent.

Finally, it has been found that the substituted cycloalkyl-carboxanilides of the formula (I) have, inter alia, a potent fungicidal activity. The new compounds can also be used in synergistic mixtures together with other, known, highly-active compounds.

Within the scope of the present invention, the substituents preferably have the following meanings:

Unless otherwise specified, halogen can denote fluorine, chlorine, bromine and iodine, preferably fluorine, chlorine and bromine.

Alkyl, alkoxy and alkylthio represent a radical which has 1-8, preferably 1-6, and particularly preferably 1-4, carbon atoms per alkyl unit, for example methyl, ethyl, n- and iso-propyl, n-, sec-, iso- and tert.-butyl, pentyl, n-hexyl or iso-hexyl, methoxy, ethoxy, n- and iso-propoxy, n-, sec-, iso- and tert.-butoxy, pentoxy and hexoxy, methylthio, ethylthio, n- and iso-propylthio, n-, sec.-, iso- and tert.-butylthio, pentylthio and hexylthio.

Halogenoalkoxy or halogenoalkylthio generally represents a straight-chain or branched hydrocarbon radical which has 1–6 carbon atoms and 1–9 identical or different halogen atoms and which is bonded via oxygen or sulphur. Radicals having 1–4 carbon atoms and 1–5 identical or different halogen atoms are preferred. Radicals having 1 or 2 carbon atoms and 1–3 identical or different halogen atoms are very particularly preferred. The following may be mentioned by way of example: trifluoromethoxy, trichloromethoxy, difluorochloromethoxy, dichlorofluoromethoxy, difluoroethoxy, trifluoroethoxy, tetrafluoroethoxy, pentafluoroethoxy, trifluoromethylthio, trichloromethylthio, difluorochloromethylthio, dichlorofluoromethylthio, difluoroethylthio, trifluoromethylthio and tetrafluoroethylthio.

Halogenoalkyl has the meaning of halogenoalkoxy, with the difference that the oxygen or sulphur atom is absent.

Cycloalkyl generally represents a cyclic hydrocarbon radical having 3–10 carbon atoms. Radicals having 3–7 carbon atoms are preferred. The following may be mentioned by way of example: cyclopropyl, cyclobutyl, cyclopentyl, cyclohexyl, cycloheptyl and cyclodecanyl.

The cycloalkyl radicals can be monosubstituted to polysubstituted. Substituents which may be mentioned are alkyl having 1–4 carbon atoms halogen, halogenoalkyl having 1 to 4 carbon atoms and 1 to 9 identical or different halogen atoms, alkoxy having 1 to 4 carbon atoms, hydroxyl and alkylcarbonyloxy having 1 to 6 carbon atoms in the alkyl moiety.

Phenyl phenylalkyl and substituted phenoxyalkyl generally represent phenyl, phenylalkyl and phenoxyalkyl in which phenyl hydrogen atoms are optionally substituted by one or more substituents $Y^{1'}$–$Y^{5'}$. In this context, $Y^{1'}$–$Y^{5'}$ have the meaning of $Y^1$, $Y^2$ and $Y^3$, as well as nitro and cyano.

Alkenyl generally represents a straight-chain or branched hydrocarbon radical having 2 to 8 carbon atoms and one or more, preferably one or two, double bonds. Lower alkenyl having 2 to 6 carbon atoms and a double bond are preferred. An alkenyl radical having 2 to 5 carbon atoms and a double bond is particularly preferred.

Formula (I) provides a general definition of the substituted cycloalkyl carboxanilides according to the invention. Preferred compounds of the formula (I) are those in X represents cyclopropyl, cyclobutyl, cyclopentyl, cyclohexyl or cycloheptyl, each of which is optionally monosubstituted to tetrasubstituted by identical or different straight-chain or branched alkyl substitutents having 1–4 carbon atoms, it being possible for the cycloalkyl radical to be monosubstituted to hexasubstituted by identical or different straight-chain or branched alkyl substituents having 1–4 carbon atoms, Hal represents fluorine, chlorine or bromine, $Y^1$, $Y^2$ and $Y^3$ are identical or different and represent hydrogen, fluorine, chlorine, bromine, straight-chain or branched alkyl having 1–4 carbon atoms, straight-chain or branched alkoxy or alkylthio having in each case 1–4 carbon atoms, or represent halogenoalkyl, halogenoalkoxy or halogenoalkylthio, each of which has 1–4 carbon atoms in the straight-chain or branched alkyl moiety and 1–5 identical or different halogen atoms, Z represents $COSR^1$ where $R^1$ represent $C_1$–$C_8$-alkyl, $C_2$–$C_8$-alkenyl, $C_1$–$C_4$-alkoxy-$C_1$–$C_4$-alkyl, $C_1$–$C_4$-alkoxy-$C_1$–$C_4$-alkoxy-$C_1$–$C_4$-alkyl, $C_1$–$C_4$-alkylthio-$C_1$–$C_4$-alkyl, each of which is optionally monosubstituted to nonasubstituted by halogen, or represent $C_3$–$C_7$-cycloalkyl which is unsubstituted or monosubstituted to pentasubstituted by identical or different substituents from the series comprising $C_1$–$C_4$-halogenoalkyl, halogen, $C_1$–$C_4$-alkyl, $C_1$–$C_4$-alkoxy, hydroxyl or $C_1$–$C_6$-alkylcarbonyloxy, or represents phenyl-$C_1$–$C_4$-alkyl which is unsubstituted or monosubstituted to pentasubstituted in the phenyl moiety by identical or different $Y^{1'}$–$Y^{5'}$, substituents, or represents phenoxyalkyl which is unsubstituted or monosubstituted to pentasubstituted in the phenyl moiety by identical or different $Y^{1'}$–$Y^{5'}$, substituents, where $Y^{1'}$–$Y^{5'}$ have the meaning of $Y^1$–$Y^3$, $NO_2$ and cyano.

Particularly preferred compounds of the formula (I) are those in which

X represents cyclopropyl, cyclobutyl, cyclopentyl, cyclohexyl or cycloheptyl, each of which is monosubstituted or disubstituted by identical or different straight-chain or branched alkyl substituents having 1–4 carbon atoms, $Y^1$, $Y^2$ and $Y^3$ are identical or different and represent hydrogen, fluorine, chlorine, bromine, methyl or trifluoromethyl and Hal represents fluorine, chlorine or bromine, Z represents $COSR^1$ where $R^1$ represent $C_1$–$C_6$-alkyl, $C_2$–$C_6$-alkenyl, $C_1$–$C_4$-alkoxy-$C_1$–$C_4$-alkyl, $C_1$–$C_4$-alkoxy-$C_1C_4$-alkoxy-C–$C_4$-alkyl, C–$C_4$-alkylthio-$C_1$–$C_2$-alkyl, or represent $C_3$–$C_7$-cycloalkyl, each of which is unsubstituted or monosubstituted to trisubstituted by identical or different substituents from the series comprising fluorine, chlorine, bromine, $C_1$–$C_2$-alkyl, $C_1$–$C_2$-alkoxy or $C_1$–$C_6$-alkylcarbonyloxy, or represents phenyl which is unsubstituted or monosubstituted to trisubstituted by identical or different substituents from the series comprising nitro, cyano, fluorine, chlorine, bromine, methyl, trifluoromethyl, trifluoromethylthio, methoxy or trifluoromethoxy, or represents phenyl-$C_1$–$C_2$-alkyl which is unsubstituted or monosubstituted to trisubstituted by identical or different substituents from the series comprising nitro, cyano, fluorine, chlorine, bromine, methyl, trifluoromethyl, trifluoromethylthio, methoxy or trifluoromethoxy, or represents phenoxy-$C_1$–$C_2$-alkyl which is unsubstituted or monosubstituted to trisubstituted by identical or different substituents from the series comprising nitro, cyano, fluorine, chlorine, bromine, methyl, trifluoromethyl, trifluoromethylthio, methoxy or trifluoromethoxy.

Very particularly preferred compounds of the formula (I) are those in which

X represents cyclopentyl or cyclohexyl, each of which is substituted in the 1-position by methyl or ethyl and each of which is optionally additionally substituted by a further alkyl radical having 1–3 carbon atoms, Hal represents fluorine, chlorine or bromine and $Y^1$, $Y^2$ and $Y^3$ are identical or different and represent hydrogen, fluorine, chlorine, bromine or trifluoromethyl, Z represents $COSR^1$, where $R^1$ represent $C_1$-$C_4$-alkyl, $C_2$-$C_5$-alkenyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, or represent $C_3$-$C_7$-cycloalkyl which is monosubstituted to trisubstituted by identical or different substituents from the series comprising methoxy, fluorine, chlorine, bromine, methyl or $C_1$-$C_4$-alkylcarbonyloxy, or represents phenyl which is monosubstituted to trisubstituted by identical or different substituents from the series comprising nitro, cyano, fluorine, chlorine, bromine, methyl or methoxy, or represents phenylmethyl which is monosubstituted to trisubstituted by identical or different substituents from the series comprising nitro, cyano, fluorine, chlorine, bromine, methyl or methoxy.

If, for example, 2,6-dichloro-4-amino-phenol, 1-methyl-1-chlorocarbonylcyclohexane and s-butyl thiocarbonate are used as starting substances, the course of the reaction can be represented by the following equation

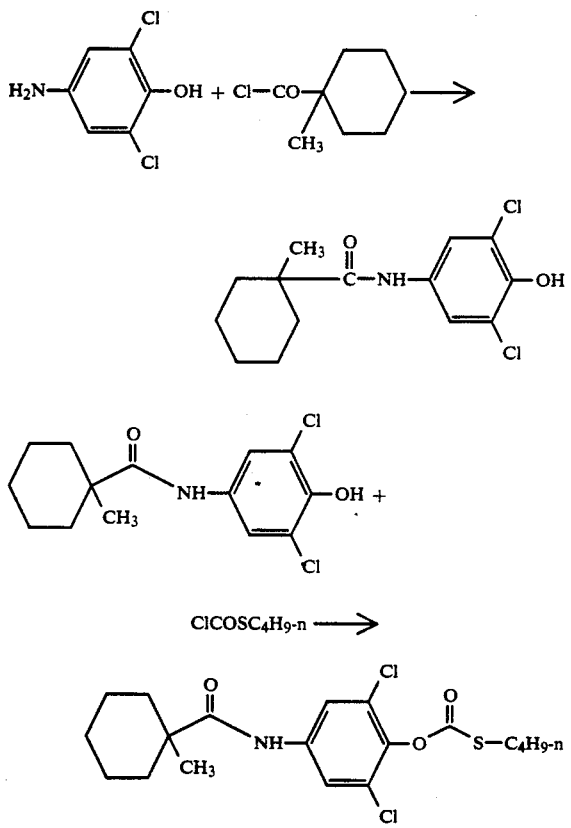

Formula (II) provides a general definition of the aminophenols required as starting substances for carrying out the process according to the invention. In this formula (II), the radicals Hal and $Y^1$-$Y^3$ have the meanings already given in connection with the description of the compounds of the formula (I) according to the invention. Most of the compounds are known and can be prepared by analogous processes (cf. "Methoden der organischen Chemie" [Methods in Organic Chemistry], Houben-Weyl, Volume VI/1c, Phenols, Part 1, Georg Thieme Verlag, Stuttgart, 1976, and "Reaktionen der organischen Synthese" [Reactions in Organic Synthe-sis], Cesare Ferri, p. 81, 89, 91, 97, 118, 120, 122, 124, 126, 128, Georg Thieme Verlag, Stuttgart, 1978).

The 4-amino-2-chloro- or -2-bromo-6-trifluoromethylphenols have been disclosed in Jp. Kokai Tokkyo Koho Jp 61/126055 and, for example, 4-amino-2,3,5,6-tetrafluorophenol is known from Zh. Org. Khim. 10(9), 1923-1927 (1974). The compounds of the formula (II A)

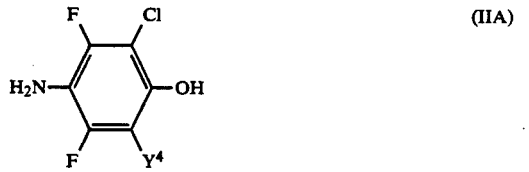

in which $Y^4$ represents fluorine or chlorine, are the subject of EP-A-293,718 and are prepared, for example, from corresponding hydroxybenzoic acids of the formula (VA)

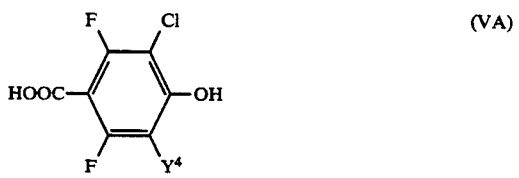

by decarboxylating the resulting phenols of the formula (VIA)

followed by nitration to give the nitro compounds of the formula (VIIA)

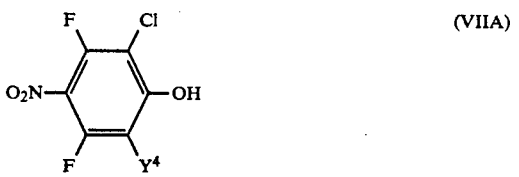

which are then hydrogenated, for example using hydrogen and Raney nickel, to give the corresponding amines of the formula (IIA).

The compounds of the formula (VIIA) are also a subject of the European Application EP-A-293,718.

Formula (III) in which X represents cycloalkyl provides a general definition of the cycloalkanecarboxylic acid derivatives furthermore required for carrying out the process according to the invention. In this formula (III), the radicals X and $Hal^1$ have the meanings already given in connection with the description of the compounds of the formula (I) according to the invention. The compounds are known and can be prepared by analogous processes (cf. Diversi et. al., Synthesis 1971, 258; U.S. Pat. No. 3,674,831; "Reaktionen der organischen Synthese" [Reactions in Organic Synthesis] Cesare Ferri, p. 460, 461, 1978, Georg Thieme Verlag, Stuttgart); Houben-Weyl, Methoden der organischen Chemie [Methods in Organic Chemistry], Vol. E5 Part 1, p. 211, 320, 343, 428, et seq., G. Thieme-Verlag, Stuttgart, 1985).

The Thio-carbonic acid derivatives of the formula (V) in which Z and Hal² have the abovementioned meaning, which furthermore for carrying out the process according to the invention, are known and can be prepared by analogous processes (cf. Georg Thieme Verlag, Stuttgart; Houben-Weyl, "Methoden der organischen Chemie, Kohlensäure-Derivate" [Methods in Organic Chemistry, Carbonic Acid Derivatives], Vol. E4, p. 30 et seq., Georg Thieme Verlag, Stuttgart, 1983).

Formula (IV) provides a definition of the acylaminophenols used as intermediates in the process according to the invention.

If appropriate, the process according to the invention is carried out in the presence of acid acceptors. Acid acceptors which can be used are all customary acid-binding agents. The following have proved themselves in particular: alkali metal carbonates and alkali metal alcoholates such as sodium carbonate and potassium carbonate, sodium methylate, sodium ethylate, potassium methylate and potassium ethylate, furthermore aliphatic, aromatic and heterocyclic amines, for example triethylamine, trimethylamine, dimethylaniline, 1,8-diazabicyclo-(5,4,0)-undec-7-ene, dimethylbenzylamine and pyridine.

For carrying out the process according to the invention, 1-2 moles, in particular 1-1.4 moles, of the compounds of the general formula (III) are preferably employed per mole of amino-phenol of the general formula (II) in the first reaction step.

For the second reaction step of the process according to the invention, 1-2 moles, in particular 1-1.4 moles, of the compounds of the general formula (V) are preferably employed per mole of acylaminophenol of the formula (IV).

Suitable diluents for carrying out the process according to the invention are virtually all inert organic diluents. These include, in particular, aliphatic and aromatic, optionally halogenated hydrocarbons such as pentane, hexane, heptane, cyclohexane, petroleum ether, benzine, ligroin, toluene, xylene, methylene chloride, ethylene chloride, chloroform, carbon tetrachloride, chlorobenzene and o-dichlorobenzene, ethers such as diethyl ether and dibutyl ether, glycol dimethyl ether and diglycol dimethyl ether, tetrahydrofuran and dioxane, ketones such as acetone, methyl ethyl ketone, methyl isopropyl ketone and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone and also dimethyl sulphoxide, tetramethylene sulphone and hexamethylphosphoric triamide.

The process according to the invention is generally carried out at temperatures between −50° C. and 120° C. The range between 0° C. and 110° C. is preferred. The reactions are generally carried out under atmospheric pressure.

Working-up is carried out by customary methods, for example by toluene extraction or methylene chloride extraction of the products from the reaction mixture which has been diluted with water, washing the organic phase with water, drying and distilling, or so-called "incipient distillation", that is to say prolonged heating under reduced pressure to moderately elevated temperatures to free the mixture from the last volatile components, or by chromatographic purification over silica gel or, for example by crystallisation. Refractive index, melting point, $R_f$ value or boiling point are used to characterise the compounds.

The active compounds according to the invention are suitable for use in pest control, in particular as fungicides.

Fungicidal agents are employed in plant protection for combating Plasmodiophoromycetes, Oomycetes, Chytridiomycetes, Zygomycetes, Ascomycetes, Basidiomycetes, Deuteromycetes.

Bactericidal agents are employed in plant protection for combating Pseudomonadaceae, Rhizobiaceae, Enterobacteriaceae, Corynebacteriaceae and Streptomycetaceae.

PREPARATION EXAMPLES

Preparation of the Starting Compounds

Example A1

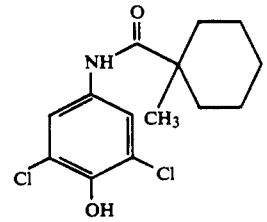

18.5 g (0.085 mol) of 4-amino-2,6-dichlorophenol are dissolved in 150 ml of tetrahydrofuran and first treated with 8.6 g (0.085 mol) of triethylamine and then, at 0° C. internal temperature, with 15 g (0.094 mol) of 1-methylcyclohexanecarboxylic acid chloride. The mixture is stirred overnight at 20° C. and another 5 g of carboxylic acid chloride and 2.8 g of triethylamine are then added to the reaction mixture to complete the reaction. After 2 hours, the mixture is poured onto ice, and the solid which has been filtered off with suction is recrystallised from toluene. The result is the abovementioned compound of a melting point of 140° C.; yield: 22.3 g (=87 % of theory).

The compounds of the formula (IV) or (IVa) are obtained analogously.

Example A2

3,5-Dichloro-2,6-difluoro-4-hydroxybenzoic acid 300 g of potassium hydroxide, 600 ml of water, 15 g of tetrabutylammonium chloride and 135 g of 3,5-dichloro-2,4,6-trifluorobenzotrifluoride are introduced in a stirring apparatus, and the mixture is then refluxed for 5 hours. When the reaction is complete, the mixture is cooled and acidified by the dropwise addition of hydrochloric acid. The solid product is filtered off with suction and dried in vacuo. Yield: 93 g of a melting point of 102°-105° C.

Example A3

3-Chloro-2,5,6-trifluoro-4-hydroxy-benzoic acid 238 g of product of a melting point of 87°-90° C. are obtained analogously to Example A1 by refluxing 400 g of NaOH, 1200 ml of water, 15 g of tetraethylammonium chloride and 276 g of 3-chlorotetrafluorobenzotrifluoride for 6 hours.

Example A4

2,6-Dichloro-3,5-difluorophenol 50 g of 3,5-dichloro-2,6-difluoro-4-hydroxybenzoic acid and 10 ml of dimethylformamide are mixed and heated. Carbon dioxide is evolved at 105°-130° C., and the reaction is allowed to come to an end at this temperature. 200 ml of toluene and then 80 ml of water are subsequently stirred in, the phases are separated, and the organic phase is dried and subsequently distilled. 34 g of the product of a boiling point of 87°-88° C. and a refractive index of $n_D^{20}$: 1.5310 are obtained.

Example A5

2-Chloro-3,5,6-trifluorophenol of a boiling point of 68°-70° C./20 mbar is obtained analogously to Example A3.

Example A6

2,6-Dichloro-3,5-difluoro-4-nitro-phenol 20 g of 2,6-dichloro-3,5-difluorophenol are introduced into 70 ml of acetic acid, and 8 g of 98% strength nitric acid are added dropwise. Stirring of the mixture is subsequently continued for 2 hours at room temperature, and the mixture is taken up in 150 ml of dichloromethane and washed twice with water. After the dichloromethane has been distilled off, 18 g of product remain. 94% pure according to GC analysis.

Example A7

2-Chloro-3,5,6-trifluoro-4-nitrophenol

Analogously to Example A5, 25 g of 2-chloro-3,5,6-trifluoro-4-nitrophenol of a purity of 93% and a melting point of 107-109° C. are obtained by nitrating 28 g of 2-chloro-3,5,6-trifluorophenol.

Example A8

2,6-Dichloro-3,5-difluoro-4-amino-phenol 18 g of 2,6-dichloro-3,5-difluoro-4-nitrophenol are hydrogenated in 100 ml of methanol in the presence of 1.5 g of Raney nickel at 25°-45° C. with 30-50 bar hydrogen until the uptake of hydrogen has ended. The solution is filtered and then freed from the solvent under reduced pressure. 13 g of aminophenol remain (GC purity 98.4%); m.p. 151° C.

Example A9

2-Chloro-3,5,6-trifluoro-4-amino-phenol

Analogously to Example A7, 20 g of aminophenol (GC purity 97%) are obtained by hydrogenation of 25 g of 2-chloro-3,5,6-trifluoro-4-nitro-phenol in 120 ml of methanol and 2 g of Raney nickel.

EXAMPLE 1

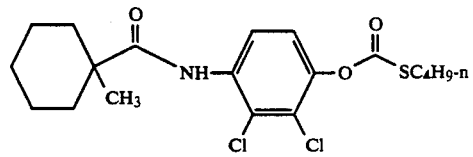

5 g (0.0165 mol) of 4-(1-methylcyclohexyl-carbonyl-2,3-dichlorophenol are dissolved in 20 ml of tetrahydrofuran and 2.5 ml (0.019 mol) of triethylamine and the mixture is added dropwise at 20° C. to 2.5 g (0.0177 mol) of thiocarbonic acid s-butyl ester chloride. The reaction solution is stirred for one hour at 50° C., cooled and poured into ice-water. The solid is filtered off with suction and dried.

Thiocarbonic acid s-butyl ester O-(2,3-dichloro-4-(1-methyl-cyclohexylcarbonyl))-phenyl ester of a melting point of m.p. 62° C. are obtained. The following are obtained analogously:

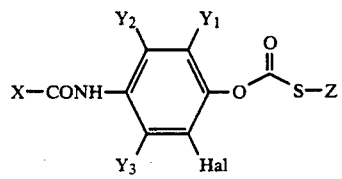

| Ex. No. | X | $Y_1$ | $Y_2$ | $Y_3$ | Hal | Z | Physical data (m.p. °C.) |
|---|---|---|---|---|---|---|---|
| 2 | ![cyclohexyl-CH3] | H | H | Cl | Cl | $CH_2CH_2-C_4H_9t$ | 66 |
| 3 | " | H | H | Cl | Cl | $CH(CH_3)C_2H_5$ | 103 |
| 4 | " | H | H | Cl | Cl | $CH_2-C_4H_9$-t | 88 |
| 5 | " | H | H | Cl | Cl | $C_3H_7$-i | 102 |
| 6 | " | H | H | Cl | Cl | $C_2H_5$ | 56 |
| 7 | " | H | H | Cl | Cl | $CH(CH_3)CH_2H_7$-i | 77 |
| 8 | " | H | H | Cl | Cl | $CH_2$-phenyl | 55 |
| 9 | " | H | H | Cl | Cl | $C_4H_9$-t | 112 |
| 10 | " | H | H | Cl | Cl | $CH_2CH_2-C_3H_7$-i | 68 |
| 11 | " | H | H | Cl | Cl | $CH_2CH_2OCH_3$ | |

-continued

| Ex. No. | X | $Y_1$ | $Y_2$ | $Y_3$ | Hal | Z | Physical data (m.p. °C.) |
|---|---|---|---|---|---|---|---|
| 12 | ⬡—$C_2H_5$ | H | H | Cl | Cl | $CH_3$ | |
| 13 | ⬡—$CH_3$ | H | Cl | H | Cl | $CH_3$ | |
| 14 | ⬡—$CH_3$ | H | H | $CH_3$ | Cl | $CH_3$ | |

EXAMPLE 20

Botrytis Test (Dwarf Bean)/Protective

Solvent: 4.7 parts by weight of acetone
Emulsifier: 0.3 parts by weight of alkyl-aryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, 2 small agar pieces on which Botrytis cinerea is growing are placed on each leaf. The inoculated plants are placed in a darkened, humid chamber at 20° C. 3 days after the inoculation, the size of lesions on the leaves is evaluated.

In this test, a clearly superior activity compared with the prior art is shown, for example, by the compounds of the following Preparation Examples:

We claim:

1. Compounds of the formula (I) in which

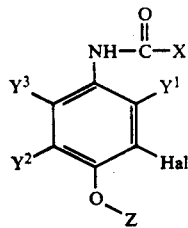

X represents cycloalkyl selected from the group consisting of cyclopropyl, cyclopentyl, cyclohexyl or cycloheptyl, it being possible for the cycloalkyl radical to be monosubstituted to hexasubstituted by identical or different straight-chain or branched alkyl substituents having 1-4 carbon atoms, Hal represents fluorine, chlorine or bromine, $Y^1$, $Y^2$ and $Y^3$ are identical or different and represent hydrogen, fluorine, chlorine, bromine, straight-chain or branched alkyl having 1-4 carbon atoms, straight-chain or branched alkoxy or alkylthio having in each case 1-4 carbon atoms, or represent halogenoalkyl, halogenoalkoxy or halogenoalkylthio, each of which has 1-4 carbon atoms in the straight-chain or branched alkyl moiety and 1-5 identical or different halogen atoms, Z represents $COSR^1$ where $R^1$ represent $C_1-C_8$-alkyl, $C_1-C_4$-alkoxy-$C_1-C_4$-alkyl, $C_1-C_4$-alkoxy-$C_1-C_4$-alkoxy-$C_1-C_4$-alkyl, $C_1-C_4$-alkylthio-$C_1-C_4$-alkyl, each of which is optionally monosubstituted to nonasubstituted by halogen, or represent $C_3-C_7$-cycloalkyl which is unsubstituted or monosubstituted to pentasubstituted by identical or different substituents from the series consisting of $C_1-C_4$-halogenoalkyl, halogen, $C_1-C_4$-alkyl, $C_1-C_4$-alkoxy hydroxyl or $C_1-C_4$-alkylcarbonyloxy, or represents phenyl-$C_1-C_4$-alkyl which is unsubstituted or monosubstituted to pentasubstituted in the phenyl moiety by identical or different $Y^{1'}-Y^{5'}$ substituents, or represents phenoxyalkyl which is unsubstituted or monosubstituted to pentasubstituted in the phenyl moiety by identical or different $Y^{1'}-Y^{5'}$ substituents, where $Y^{1'}-Y^{5'}$ have the meaning of $Y^1-Y^3$, $NO_2$ and cyano.

2. Compounds of the formula (I) according to claim 1, in which

X represents cyclopropyl, cyclobutyl, cyclopentyl, cyclohexyl or cycloheptyl, each of which is monosubstituted or disubstituted by identical or different straight-chain or branched alkyl substituents having 1-4 carbon atoms, $Y^1$, $Y^2$ and $Y^3$ are identical or different and represent hydrogen, fluorine, chlorine, bromine, methyl or trifluoromethyl and Hal represents fluorine, chlorine or bromine, Z represent $COSR^1$ where $R^1$ represent $C_1-C_6$-alkyl, $C_2-C_6$-alkenyl, $C_1-C_4$-alkoxy-$C_1-C_4$-alkyl, $C_1-C_4$-alkoxy-$C_1-C_4$-alkoxy-$C_1-C_4$-alkyl, $C_1-C_4$-alkylthio-$C_1-C_2$-alkyl, or represent $C_3-C_7$-cycloalkyl, each of which is unsubstituted or monosubstituted to trisubstituted by identical or different substituents from the series, consisting of fluorine, chlorine, bromine, $C_1-C_2$-alkyl, $C_1-C_2$-alkoxy or $C_1-C_6$-alkylcarbonyloxy, or represent phenyl which is unsubstituted or monosubstituted to trisubstituted by identical or different substituents from the series consisting of nitro, cyano, fluorine, chlorine, bromine, methyl, trifluoromethyl, trifluoromethylthio, methoxy or trifluoromethoxy, or represent phenyl-$C_1-C_2$-alkyl which is unsubstituted or monosubstituted to trisubstituted by identical or different substituents from the series consisting of nitro, cyano, fluorine, chlorine, bromine, methyl, trifluoromethyl, trifluoromethylthio, methoxy or trifluoromethoxy, or represent phenoxy-$C_1$-$C_2$-alkyl which is unsubstituted or monosubstituted to trisubstituted by identical or different substituents from the series consisting of nitro, cyano, fluorine, chlorine, bromine, methyl, trifluoromethyl, trifluoromethylthio, methoxy or trifluoromethoxy.

3. Compounds of the formula (I) according to claim 1, in which

X represents cyclopentyl or cyclohexyl, each of which is substituted in the 1-position by methyl or ethyl and each of which is optionally additionally substituted by a further alkyl radical having 1-3 carbon atoms, Hal represents fluorine, chlorine or bromine and $Y^1$, $Y^2$ and $Y^3$ are identical or different and represent hydrogen, fluorine, chlorine, bromine or trifluoromethyl, Z represents $COSR^1$, where $R^1$ represent $C_1$-$C_4$-alkyl, $C_2$-$C_5$-alkenyl, $C_1$-$C_4$-alkoxy-$C_1$-$C_4$-alkyl, $C_1$-$C_4$-alkoxy-$C_1$-$C_4$-alkoxy-$C_1$-$C_4$-alkyl, or represent $C_3$-$C_7$-cycloalkyl which is monosubstituted to trisubstituted by identical or different substituents from the series consisting of methoxy, fluorine, chlorine, bromine, methyl or $C_1$-$C_4$-alkylcarbonyloxy, or represents phenyl which is monosubstituted to trisubstituted by identical or different substituents from the series consisting of nitro, cyano, fluorine, chlorine, bromine, methyl or methoxy, or represents phenylmethyl which is monosubstituted to trisubstituted by identical or different substituents from the series consisting of nitro, cyano, fluorine, chlorine, bromine, methyl or methoxy.

4. Pesticides, characterised in that they contain at least one compound of the formula (I) according to claim 1.

5. Method of combating pests, characterised in that at least one compound of the formula (I) according to claim 1 is allowed to act on pests and/or their environment.

* * * * *

UNITED STATES PATENT AND TRADEMARK OFFICE
CERTIFICATE OF CORRECTION

PATENT NO. : 5,250,568
DATED : October 5, 1993
INVENTOR(S) : Kruger, et al.

It is certified that error appears in the above-indentified patent and that said Letters Patent is hereby corrected as shown below:

Col. 11, line 56  After " cyclopropyl," insert -- cyclobutyl,--

Col. 12, line 23  After " $C_1$-$C_8$-alkyl, " insert -- $C_2$-$C_8$-alkenyl --

Col. 12, line 31  After " or $C_1$ - " delete " $C_4$ " and substitute -- $C_6$ --

Signed and Sealed this

Fourth Day of April, 1995

Attest:

BRUCE LEHMAN

*Attesting Officer*           *Commissioner of Patents and Trademarks*